United States Patent [19]

Veber

[11] 4,139,526
[45] Feb. 13, 1979

[54] SOMATOSTATIN ANALOGS

[75] Inventor: Daniel F. Veber, Ambler, Pa.

[73] Assignee: Merck & Co., Inc., Rahway, N.J.

[21] Appl. No.: 856,364

[22] Filed: Dec. 1, 1977

[51] Int. Cl.$^2$ .................... C07C 103/52; A61K 37/00
[52] U.S. Cl. .............................. 260/112.5 S; 424/177
[58] Field of Search .................... 424/177; 260/112.55

[56] References Cited
U.S. PATENT DOCUMENTS 3,997,517  12/1976  Sarantakis ........................... 424/177

OTHER PUBLICATIONS

Sarantakis, et al., Biochem. Res. Comm., 75, 143–148 (1977).

*Primary Examiner*—Delbert R. Phillips
*Attorney, Agent, or Firm*—Walter Patton; Harry E. Westlake, Jr.

[57] ABSTRACT

Bicyclic somatostatin analogs and pharmaceutically acceptable non-toxic acid addition salts thereof are prepared by the solid phase method. These analogs have the property of inhibiting the release of insulin, glucagon and growth hormone in humans and animals. The compounds are particularly useful in the treatment of diabetes. Due to the bicyclic structure, these analogs are resistant to enzymatic metabolism and have a longer duration of activity.

13 Claims, No Drawings

SOMATOSTATIN ANALOGS

BACKGROUND OF THE INVENTION

Somatostatin is a tetradecapeptide having the structure:

Ala—Gly—Cys—Lys—Asn—Phe—Phe—Trp—Lys—Thr—Phe—Thr—Ser—Cys—OH and has the properties of inhibiting the release of growth hormone, inhibiting the release of insulin and glucagon and reducing gastric secretion. Somatostatin itself has a short duration of action because it is inactivated, inter alia, by aminopeptidases and carboxypeptidases present in vivo. This problem of the short duration of action has been partially solved in the prior art by preparing derivatives of somatostatin which have low solubility, thus attaining a slow release on subcutaneous injection. Once dissolved, however, the derivatives are no more stable to inactivation by aminopeptidases and carboxypeptidases than somatostatin itself. The present invention provides bicyclic somatostatin analogs having higher biological activities and a longer duration of action than somatostatin and a novel method for preparing said analogs.

SUMMARY OF THE INVENTION

This invention is concerned with novel bicyclic somatostatin analogs having a more potent biological activity and a longer duration of action than naturally occurring somatostatin having the structural formulas:

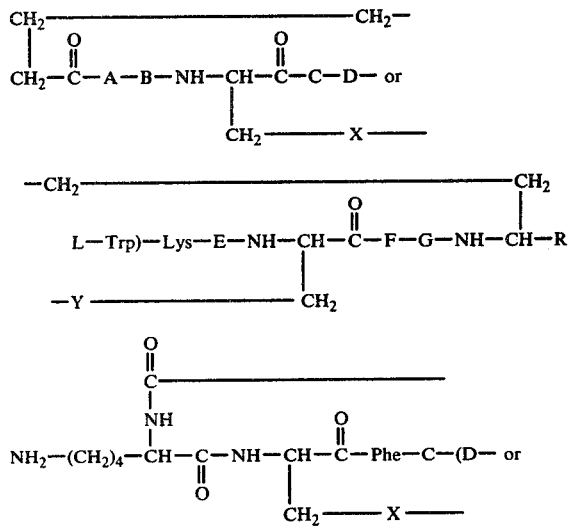

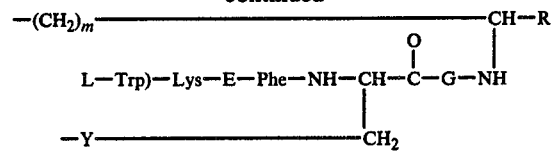

wherein,
R is H or COOH,
m is 0 to 9,
A is $(Lys)_n$,
B is $(Asn)_p$, Abu, Pro or Ala,
C is Phe or Tyr,
E is Thr or Val,
F is $(Thr)_q$ or Val,
G is $(Ser)_r$, Pro, Ala or Gly, and
X and Y are independently $CH_2$—S or S wherein n, p, q and r are 0 or 1 and pharmaceutically acceptable non-toxic acid addition salts thereof.

The preferred bicyclic somatostatin analogs of the present invention are illustrated by the following structural formula:

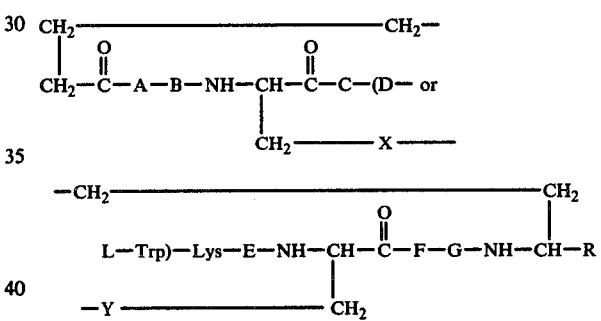

wherein,
R is H or COOH,
A is $(Lys)_n$,
B is $(Asn)_p$, Abu, Pro or Ala,
C is Phe or Tyr,
E is Thr or Val,
F is $(Thr)_q$ or Val,
G is $(Ser)_r$, Pro, Ala or Gly, and
X and Y are independently $CH_2$—S or S wherein n, p, q and r are 0 or 1 and pharmaceutically acceptable non-toxic acid addition salts thereof. Preferred compounds are those wherein n, p, q and r are 0.

Included in the present invention are compounds having the structural formula:

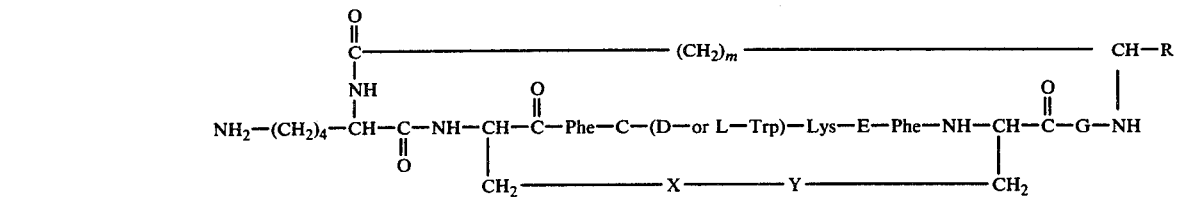

wherein,
R is H or COOH, m is 0 to 9,
C is Phe or Tyr,
E is Val or Thr,
G is Ser, Pro, Ala or Gly, and
X and Y are independently CH$_2$—S or S
and pharmaceutically acceptable non-toxic acid addition salts thereof.

Still further preferred bicyclic somatostatin analogs are those having the structural formula:

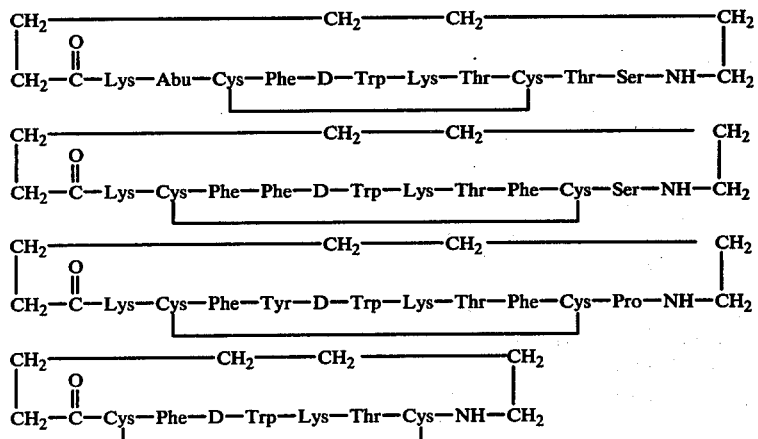

and the pharmaceutically acceptable non-toxic acid addition salts thereof.

Included in the present invention are the monocyclic (Acm)Cys containing therapeutically useful intermediates having the structural formula:

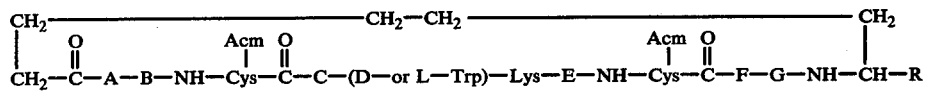

wherein,
R is H or COOH,
A is (Lys)$_n$,
B is (Asn)$_p$, Abu, Pro or Ala,
C is Phe or Tyr,
E is Thr or Val,
F is (Thr)$_q$ or Val,
G is (Ser)$_r$, Pro, Ala or Gly, and
X and Y are independently CH$_2$—S or S wherein n, p, q and r are 0 or 1 and pharmaceutically acceptable non-toxic acid addition salts thereof.

Included in the present invention are the monocyclic (Acm)Cys containing therapeutically useful intermediates having the structural formula:

wherein
R is H or COOH,
m is 0 to 9,
C is Phe or Tyr,
E is Val or Thr,
G is Ser, Pro, Ala or Gly
and the pharmaceutically acceptable non-toxic acid addition salts thereof.

Illustrative of acid addition salts are hydrochloride, hydrobromide, sulfate, phosphate, maleate, acetate, citrate, benzoate, succinate, malate, ascorbate and the like. The acid addition salts can be conveniently prepared by dissolving the above novel compounds in water, adding two equivalents of appropriate acid and lyophilizing.

The bicyclic somatostatin analogs of the present invention differ from somatostatin by virtue of the fact that they have a covalent bond between the side chains of two amino acids within the macrocyclic ring. This novel feature can be illustrated by reference to the structure of somatostatin.

Somatostatin is a tetradecapeptide having the structure:

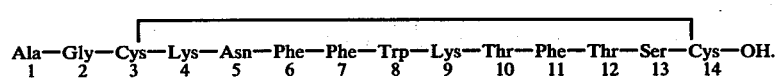

The portion of somatostatin extending from amino acid Cys[3] to Cys[14] forms a cyclic dodecapeptide of the following structure:

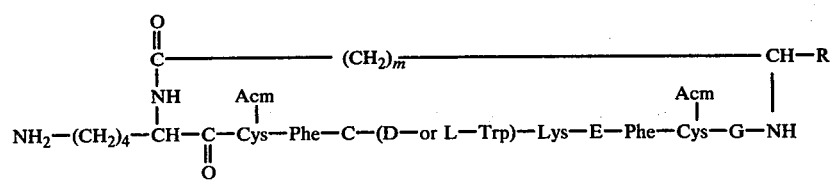

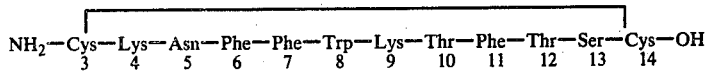

This cyclic dodecapeptide is referred to as the macrocyclic ring of somatostatin. The macrocyclic rings of the compounds of the present invention are illustrated by the fllowing structural formulas:

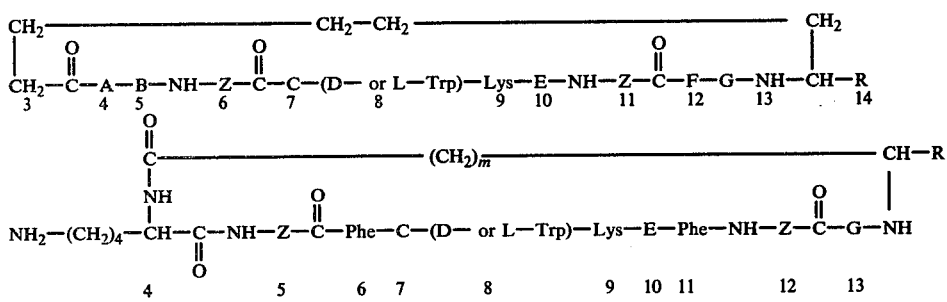

wherein R, m, A, B, C, E, F, G, X, Y, n, p, q and r are as defined above and Z is Cys, Hcy, (Acm)Cys or (Acm)Hcy. These rings will also be referred to below as Ring I. The removal of the Acm protecting groups from the Cys, or Hcy amino acids within the macrocyclic ring followed by oxidation of the sulfhydryl groups results in formation of Rings II and III. The ring structure formed by amino acids 7 to 10 of Ring I and the side groups of amino acids 6 and 11 joined by a disulfide bond or by amino acids 6 to 11 of Ring I and the side groups of amino acids 5 and 12 joined by a disulfide bond is designated Ring II. When Cys or Hcy are at positions 6 and 11 of Ring I, the amino acids at position 7 to 10 of Ring I are common to both Rings I and II. When Cys or Hcy are at positions 5 and 12 of Ring I, the amino acids at position 6 to 11 of Ring I are common to both Rings I and II. The ring structure formed by the amino acids of Ring I (not commonly shared by Ring I and II) and the side groups of amino acids 6 and 11 or 5 and 12 joined by a disulfide bond is designated Ring III.

In the bicyclic somatostatin analogs of the present invention the $Ala^1$-$Gly^2$ and the amino group of $Cys^3$ of somatostatin are deleted.

The present invention includes bicyclic somatostatin analogs wherein $Lys^4$ is deleted. Furthermore, the bicyclic somatostatin analogs of the present invention include those wherein $Asn^5$ is deleted or replaced by α-aminobutyric acid, Pro or Ala; $Phe^7$ is replaced by Tyr; $Trp^8$ is replaced by D-Trp; $Thr^{10\ and\ 12}$ are independently replaced by Val; and $Ser^{13}$ is replaced by Pro, Ala or Gly.

The bicyclic somatostatin analogs of the present invention differ from somatostatin by virtue of the fact that they lack an N-terminal amino group thus eliminating the group involved in enzymic cleavage of the molecule by aminopeptidases. Further stability is attained by the formation of Rings II and III as described above. The presence of these rings increases the rigidity of the molecule and reduces its susceptibility to enzymatic metabolism. Generally, very few peptidases cleave peptides at cystine residues. Therefore, the analogs of the present invention are more resistant to cleavage in vivo than somatostatin and thus have a prolonged duration of action.

The abbreviated designations, which are used herein for the amino acid components, certain preferred protecting groups, reagents and solvents employed in the process of this invention are as follows:

TABLE I

| Abbreviated Designation | Amino Acid |
|---|---|
| Lys | L-lysine |
| Phe | L-phenylalanine |
| Trp | L-tryptophan |
| D-Trp | D-tryptophan |
| Thr | L-threonine |
| Aha | 7-aminoheptanoic acid |
| Tyr | L-tyrosine |
| Val | L-valine |
| Abu | L-α-aminobutyric acid |
| Ser | L-serine |
| Asn | L-asparagine |
| Pro | L-proline |
| Asu | D- or L-α-aminosuberic acid |
| Hcy | L-homocysteine |
| Cys | L-cysteine |
| Abbreviated Designation | Protecting Groups |
| INOC | isonicotinyloxycarbonyl |
| BOC | tert-butyloxycarbonyl |
| OMe | methyl ester |
| tBu | tert-butyl |
| CBZ | benzyloxycarbonyl |
| Bzl | benzyl |
| 2-Cl-CBZ | 2-chlorobenzyloxycarbonyl |
| Acm | acetamidomethyl |
| Abbreviated Designation | Activating Groups |
| ONp | p-nitrophenyl ester |
| HSE | N-hydroxysuccinimide ester |
| HBT | 1-hydroxybenzotriazole |
| Abbreviated Designation | Condensing Agents |
| DCCI | dicyclohexylcarbodiimide |
| Abbreviated Designation | Reagents |
| TFA | trifluoroacetic acid |
| TEA | triethylamine |
| DIPEA | diisopropylethylamine |
| Abbreviated Designation | Solvents |
| EPAW | ethyl acetate-pyridine-acetic acid-water |
| BAW | butanol-acetic acid-water |
| CMW | chloroform-methanol-water |
| DMF | dimethylformamide |
| THF | tetrahydrofuran |

In accordance with the present invention, Ring I of the novel bicyclic somatostatin analogs is prepared by cyclizing corresponding linear peptides. The linear peptides are prepared by using the solid phase sequential synthesis technique. Accordingly, the process for preparing Ring I of the bicyclic somatostatin analogs of the present invention comprises (a) preparing a corresponding blocked linear peptide attached to a solid phase resin; (b) selectively deblocking the N-terminal amine group; (c) removing the linear peptide from the resin; (d) treating the linear peptide with a cyclizing agent to obtain Ring I of the bicyclic peptide through the formation of an amide bond.

Rings II and III are formed by removing the remaining blocking groups and oxidizing the sulfhydryl groups of Cys or Hcy within the macrocyclic Ring I. The bicyclic structure is thereby generated through the formation of the disulfide bond. The relative location of the Cys or Hcy amino acids in Ring I determines the location and size of Rings II and III.

When the linear peptide is prepared on the resin, it is not critical which amino acid is selected to be at the C-terminal position provided only that the sequence of amino acids in the linear peptide corresponds to that in the desired somatostatin analog. Once a linear peptide has been cyclized one can no longer determine which amino acid was at the C-terminus of the linear peptide. As an example to illustrate this, either of the two following linear peptides, when cyclized, will give the identical Ring I of the bicyclic somatostatin analog:
D-Trp-(ε-2-Cl-CBZ)Lys-(O-Bzl)Thr-(Acm)Cys-(O-Bzl)Thr-(O-Bzl)Ser-Aha-(ε-2-Cl-(CBZ)Lys-Abu-(Acm)Cys-Phe-N₃ or Aha—(ε-2-Cl—CBZ)Lys—Abu—(Acm)Cys—Phe—D—Trp—(ε-2-Cl—CBZ)—
Lys—(O—Bzl)Thr—(Acm)Cys—(O—Bzl)Thr—(O—Bzl)Ser—N₃
  ↓ cyclization
cyclo[Aha—(ε-2-Cl—CBZ)Lys—Abu—(Acm)Cys—Phe—D—Trp—(ε-2-Cl—
CBZ)Lys—(O—Bzl)Thr—(Acm)Cys—(O—Bzl)Thr—(O—Bzl)Ser].

It is evident that since the linear peptide is going to be cyclized, it does not matter which amino acid is used to start the chain. Starting with Phe at the carboxyl end, as illustrated in the first of the two examples above, has an advantage over the second example. In the first example, D-Trp, which can react with t-butyl carbonium ions formed when BOC groups are removed, is the N-terminal amino acid and thus will be added last and hence will be subjected to the least amount of exposure to t-butyl carbonium ions.

In the case wherein R is COOH, it is preferable to employ the peptide having the amino acid sequence in the second example with the exception that Aha is replaced by α-Asu. The process for preparing the required linear peptide azide may be illustrated by the following scheme:

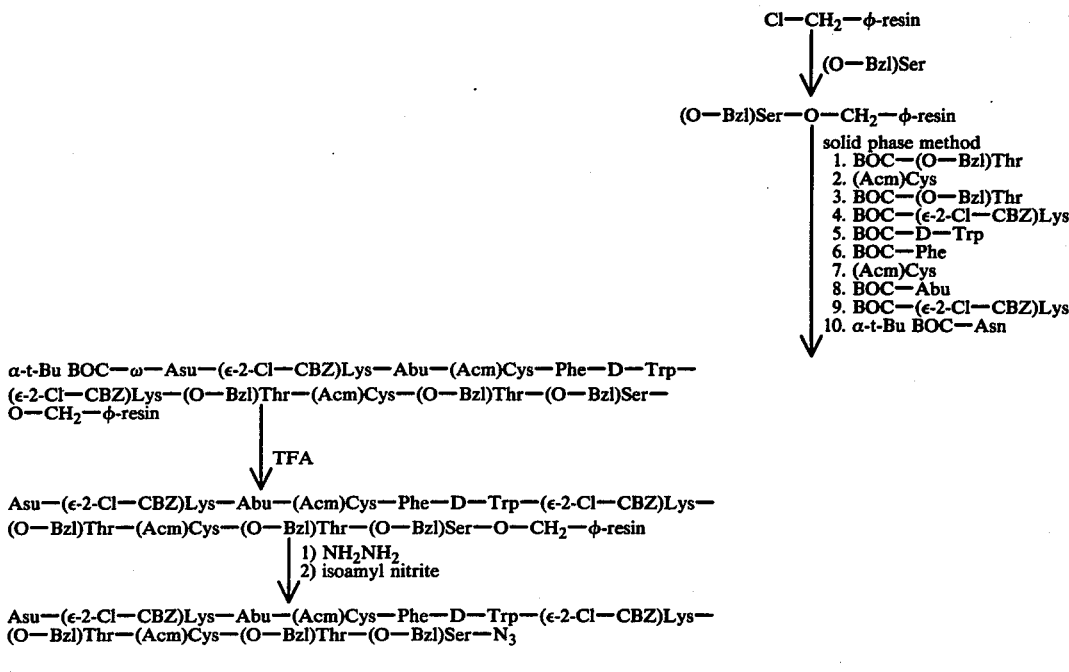

The synthesis of the linear peptides by the solid phase technique is conducted in a stepwise manner on chloromethylated resin. The resin is composed of fine beads (20-70 microns in diameter) of a synthetic resin prepared by copolymerization of styrene with 1 to 2 percent divinylbenzene. The benzene rings in the resin are chloromethylated in a Friedel-Crafts reaction with chloromethyl methyl ether and stannic chloride. The Friedel-Crafts reaction is continued until the resin contains 0.5 to 5 mmoles of chlorine per gram of resin.

The amino acid selected to be the C-terminal amino acid of the linear peptide is converted to its amino protected derivative. The carboxyl group of the selected C-terminal amino acid is bound covalently to the insoluble polymeric resin support, as for example, as the carboxylic ester of the resin-bonded benzyl chloride present in chloromethyl-substituted polystyrene-divinylbenzene resin. After the amino protecting group is removed, the amino protected derivative of the next amino acid in the sequence is added along with a coupling agent, such as dicyclohexylcarbodiimide. The amino acid reactant may be employed in the form of a carboxyl-activated amino acid such as the ONp ester, an amino acid azide, and the like. Deprotection and addition of successive amino acids is performed until the desired linear peptide is formed.

The selection of protecting groups is, in part, dictated by particular coupling conditions, in part by the amino acid and peptide components involved in the reaction.

Amino-protecting groups ordinarily employed include those which are well known in the art, for example, urethane protecting substituents such as benzyloxycarbonyl (carbobenzoxy), p-methoxycarbobenzoxy, p-nitrocarbobenzoxy, t-butyloxycarbonyl, and the like. It is preferred to utilize t-butyloxycarbonyl (BOC) for protecting the α-amino group in the amino acids undergoing reaction at the carboxyl end of said amino acid. The BOC protecting group is readily removed following such coupling reaction and prior to the subsequent step by the relatively mild action of acids (i.e., trifluoro acetic acid, or hydrogen chloride in ethyl acetate).

The -OH group of Thr and Ser can be protected by the Bzl group and the ε-amino group of Lys can be protected by the INOC group or the 2-chlorobenzyloxycarbonyl (2-Cl-CBZ) group. In the case of Lys, it is preferred to protect the ε-amino group with 2-Cl-CBZ group as this group is removed simultaneously with the Bzl groups by treatment with HF after the linear peptide has been cyclized. The INOC group is not removed by HF and requires an additional treatment with Zn. Neither group is affected by TFA, used for removing BOC protecting groups.

The sulfhydryl groups of Cys and Hcy are protected by Acm. After the linear peptide is cyclized to form Ring I, the protective groups, such as 2-Cl-CBZ and Bzl, are removed by treatment with HF. A particular advantage in using the Acm group is that, it is stable to HF and therefore remains intact after the formation of Ring I and before the formation of Rings II and III. This allows the purification of the intermediate monocyclic compound prior to removal of the Acm group and oxidation of the sulfhydryl groups to form Rings II and III.

After the linear peptide has been formed on the solid phase resin, it may be removed from the resin by a variety of methods which are well known in the art. For example, the peptide may be cleaved from the resin with hydrazine and thus directly form the peptide hydrazide which may be subsequently cyclized via the azide to the desired Ring I of the bicyclic peptide. The hydrazide is converted to the corresponding azide by reaction with a reagent which furnishes nitrous acid in situ. Suitable reagents for this purpose include a lower alkyl nitrite (e.g. t-butyl nitrite, isoamyl nitrite) or an alkali metal nitrite salt (e.g., sodium nitrite, potassium nitrite) in the presence of a strong acid such as hydrochloric, phosphoric, etc. This reaction is carried out in the presence of either water and/or a non-aqueous solvent such as dimethylformamide, tetrahydrofuran, dioxane, chloroform, methylene chloride, etc., at a temperature between about −40° C. and +20° C. Alternatively, the peptide may be removed from the resin by treatment with a lower alcohol such as methanol in the presence of an organic base such as triethylamine, thus resulting in the formation of the corresponding lower alcohol ester of the linear peptide. The resulting ester may be converted to the hydrazide which may then be cyclized, via the azide, to the desired Ring I of the bicyclic peptide. The preferred method for cleaving the peptide from the resin in the present invention is the use of hydrazine.

Rings II and III of the bicyclic somatostatin analogs are prepared by removing the Acm protecting group from the sulfhydryl groups of Cys or Hcy and oxidizing the sulfhydryl groups to disulfide. This is accomplished by $I_2$ in acetic acid or alternately by mercuric ion followed by air oxidation.

As reference to Table II will show, one preferred overall procedure for preparing the desired bicyclic peptides of the present invention involves the stepwise synthesis of the linear peptide on a solid phase resin. More specifically, in the process for preparing:

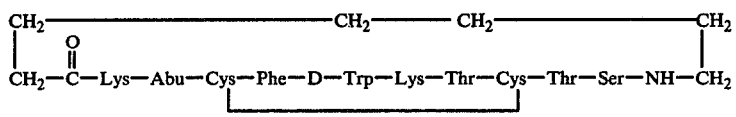

the carboxyl end of the N-blocked amino acid phenylalanine is bound covalently to an insoluble polymeric resin support as the carboxylic acid ester of the resin-bonded benzyl chloride. The amino group of Phe is protected by the BOC group. After the attachment of the Phe is completed on the resin, the protecting group BOC is removed by treatment with TFA in $CH_2Cl_2$. The subsequent amino acids are attached, in the form of BOC-amino acid, using DCCI as the condensing agent or an active ester such as ONp. After the desired linear peptide has been prepared, the N-terminal amino group is selectively deblocked and the peptide is removed from the resin by treatment with hydrazine. The resulting linear peptide hydrazide with the N-terminal amino group deblocked having the amino acid sequence: D-Trp-(ε-2-Cl-CBZ)Lys-(O-Bzl)Thr-(Acm)Cys-(O-Bzl)Thr-(O-Bzl)Ser-Aha-(ε-2-Cl-CBZ)Lys-Abu-(Acm)Cys-Phe-NH-NH$_2$ is treated with isoamyl nitrite in acid pH to form the corresponding azide. The azide solution is diluted with solvent and neutralized with an organic base. The linear peptide cyclizes to form Ring I, i.e. cyclo-[Aha-(ε-2-Cl-CBZ)Lys-Abu-(Acm)Cys-Phe-D-Trp-(ε-2-Cl-CBZ)Lys-(O-Bzl)Thr-(Acm)Cys-(O-Bzl)Thr-(O-Bzl)Ser]. During the cyclization the "pH" is checked and maintained at neutral by the addition of organic base. The "pH" in organic solvent is determined by the application of an aliquot of the solution to moistened narrow range pH paper.

After the linear peptide is cyclized to form Ring I, the protective groups, 2-Cl-CBZ and Bzl, are removed by treatment with HF in the presence of anisole. The crude cyclic peptide obtained is purified by chromatography, preferably on Sephadex eluted with 50% aqueous acetic acid and Sephadex eluted with 2N acetic acid.

Treatment of Ring I with $I_2$ in acetic acid results in the removal of the Acm protecting groups from Cys sulfhydryl groups and the formation of Rings II and III by the oxidation of the sulfhydryl groups to form a disulfide bond.

The following Examples illustrate methods of carrying out the present invention, but it is to be understood that these Examples are given for purposes of illustration and not of limitation. It is to be understood that changing the amino acid sequence of the polypeptide in accordance with the instructions provided by this disclosure, affords each of the compounds embraced by the description presented herein and embraced by claims of this application.
TABLE II
General Scheme for Preparing
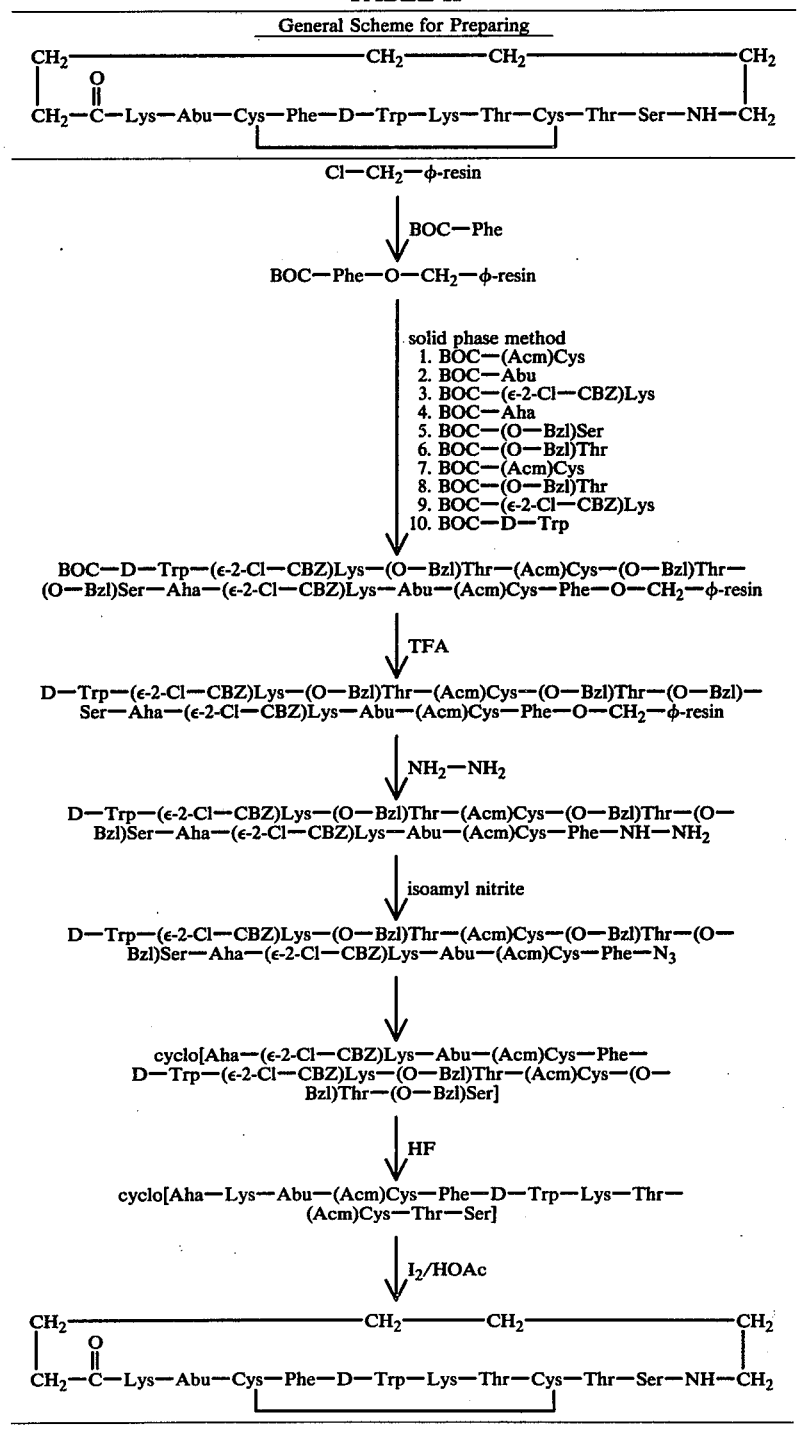
EXAMPLE 1
Preparation of
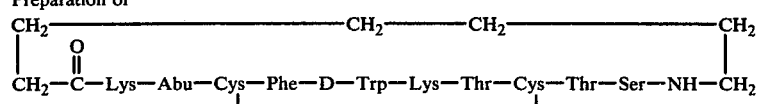
Step a) - Preparation of D—Trp—(ε-2-Cl—CBZ)Lys—(O—Bzl)Thr—(Acm)Cys—(O—Bzl)Thr—(O—Bzl)Ser—Aha—(ε-2-Cl—CBZ)Lys—Abu—(Acm)Cys—Phe—O—CH₂—φ-resin Chloromethyl resin (2% cross-linked Merrifield resin), 862.0 g. (2.37 moles), having 2.75 meq. chlorine/g., and 607.0 g. (2.37 moles, 1 equivalent) of BOC-Phe were added to 4320 ml. of peroxide-free tetrahydrofuran. The mixture was stirred in an oil bath at 80° C. bath temperature for 45 minutes. Triethylamine, 310.0 ml., was added and the reaction mixture stirred at 80° C. bath temperature for 70 hours, cooled to 25° C. and transferred to a stirred solid phase reaction column with 2000 ml. of tetrahydrofuran. After removal of the solvent, the resin was washed using the stirred column with:

3 × 2000 ml. of tetrahydrofuran
4 × 5170 ml. of ethanol
1 × 5170 ml. of acetic acid
3 × 5170 ml. of water
3 × 5170 ml. of methanol
3 × 5170 ml. of chloroform.

The BOC-Phe-O-CH$_2$-$\phi$-resin was dried in vacuo at 25° C. for 16 hours, giving 1203 g. of BOC-Phe-O-CH$_2$-$\phi$-resin containing 0.937 mmole of phenylalanine/g. of resin.

BOC-Phe-O-CH$_2$-$\phi$-resin (2.13 g.; 2.0 mmole) was carried through the procedures in Tables III and IV using 2 deblockings (2 minutes and 25 minutes) with 25% TFA in methylene chloride in the presence of 1% ethanedithiol (except when deblocking BOC-Phe-O-CH$_2$-$\phi$-resin), and 2.5 equivalents of BOC-amino acid in the required sequence until the desired BOC-undecapeptide-O-CH$_2$-$\phi$-resin was obtained.

DCCI was used as the sole coupling agent in every step except the coupling of BOC-(O-Bzl)Ser to Aha-($\epsilon$-2-Cl-CBZ)Lys-Abu-(Acm)Cys-Phe-O-CH$_2$-$\phi$-resin in which case the coupling was carried out with DCCI in the presence of 1-hydroxybenzotriazole monohydrate (HBT.H$_2$O).

The coupling of each amino acid proceeded smoothly. Best yields were obtained when the coupling was repeated in each step. When the coupling was repeated, the initial two chloroform washes, the deblocking step and the succeeding three chloroform washes were all omitted and replaced by a single chloroform wash.

The coupling reactions were carried out in methylene chloride, freshly degassed DMF or a mixture of these two solvents. The N-terminal amino group was blocked with a BOC group in each case; the hydroxy group of Thr and Ser was blocked with Bzl; the $\epsilon$-amino group of Lys with 2-Cl-CBZ and the sulfhydryl group of Cys with Acm.

When the desired BOC-undecapeptide-O-CH$_2$-$\phi$-resin was obtained, the N-terminal BOC group was removed by the terminal deblocking procedure set forth in Table V.

TABLE IV

| Protected Amino Acid | Solvent ml. |
|---|---|
| BOC-(Acm)Cys (1.46 g.) | DMF, 5 ml. CH$_2$Cl$_2$, 20 ml. |
| recouple | |
| BOC-Abu (1.02 g.) | CH$_2$Cl$_2$, 25 ml. |
| recouple | |
| BOC-($\epsilon$-2-Cl-CBZ)Lys (2.08 g.) | CH$_2$Cl$_2$, 25 ml. |
| recouple | |
| BOC-Aha (1.23 g.) | CH$_2$Cl$_2$, 25 ml. |
| recouple | |
| BOC-(O-Bzl)Ser (1.48 g.) + HBT.H$_2$O (1.53 g.) | DMF, 25 ml. |
| recouple | |
| BOC-(O-Bzl)Thr (1.55 g.) | CH$_2$Cl$_2$, 25 ml. |
| recouple | |
| BOC-(Acm)Cys (1.46 g.) | DMF, 5 ml. CH$_2$Cl$_2$, 20 ml. |
| recouple | |
| BOC-(O-Bzl)Thr (1.55 g.) | CH$_2$Cl$_2$, 25 ml. |
| recouple | |
| BOC-($\epsilon$-2-Cl-CBZ)Lys (2.08 g.) | CH$_2$Cl$_2$, 25 ml. |
| recouple | |
| BOC-D-Trp (1.52 g.) | DMF, 5.5 ml. CH$_2$Cl$_2$, 19.5 ml. |
| recouple | |

TABLE V
TERMINAL DEBLOCKING PROGRAM

| Solvent or reagent (number of treatments or washes) | CHCl$_3$ (1) | 25% TFA in CH$_2$Cl$_2$ + 1% Ethanedithiol (2) | CHCl$_3$ (3) | MeOH (2) CH$_2$Cl$_2$ (1) MeOH (2) CH$_2$Cl$_2$ (2) |
|---|---|---|---|---|
| Vol. in ml. | 40 | 40 | 40 | 40 |
| Time in minutes | 5 | 2 and 25 | 2 | 2 |

After the procedures of Tables III, IV and V were completed, the blocked undecapeptide-O-CH$_2$-$\phi$-resin was dried overnight in vacuo and weighed 5.33 g.

Step b) - Preparation of
D-Trp-($\epsilon$-2-Cl-CBZ)Lys-(O-Bzl)Thr-(Acm)Cys-(O-Bzl)Thr-(O-Bzl)Ser-Aha-($\epsilon$-2-Cl-CBZ)Lys-Abu-(Acm)Cys-Phe-NH-NH$_2$ To a mixture of 5.2 g. D-Trp-($\epsilon$-2-Cl-CBZ)Lys-(O-Bzl)Thr-(Acm)Cys-(O-Bzl)Thr-(O-Bzl)Ser-Aha-($\epsilon$-2-Cl-CBZ)Lys-Abu-(Acm)Cys-Phe-O-CH$_2$-$\phi$-resin in 50 ml. freshly degassed DMF was added 5.0 ml. NH$_2$-NH$_2$. The mixture was magnetically stirred at room temperature for 1 hour. The mixture was filtered to remove the resin. The resin was washed with 4 × 15 ml. DMF. The filtrate and washings were concentrated in vacuo to near dryness. The semi-solid residue was triturated with ether to obtain a solid. The solid was collected by filtration, and dried in vacuo for 30 min. to yield 3.50 g. crude product. The solid was slurried with

TABLE III

| Solvent or reagent (number of treatments or washes) | CHCl$_3$ (2) | 25% TFA in CH$_2$Cl$_2$ + 1% ethanedithiol (2)* | CHCl$_3$ (3) | NEt$_3$-CH$_2$Cl$_2$ (1:9) (2) | CHCl$_3$ (3) CH$_2$Cl$_2$ (3) | BOC AA in CH$_2$Cl$_2$, DMF or a mixture of both | 0.5M DCCI in CH$_2$Cl$_2$ | DMF (1) MeOH (1) DMF (1) MeOH (1) CHCl$_3$ (2) |
|---|---|---|---|---|---|---|---|---|
| Volume in ml. | 40 | 40 | 40 | 40 | 40 | 25 | 10 | 40 |
| Time in min. | 5 | 2 and 25 | 2 | 5 and 5 | 2 | 5 | 5 coupling 30 | 2 |

*1% ethanedithiol is present except in the deblocking of BOC-Phe-O-CH$_2$-$\phi$-resin 4 × 30 ml. water to remove all traces of formylhydrazide and dried in vacuo overnight to give 2.67 g. of product.

Step c) - Preparation of D-Trp-(ε-2Cl-CBZ)-Lys-(O-Bzl)Thr-(Acm)Cys-(O-Bzl)Thr-(O-Bzl)Ser-Aha-(ε-2-Cl-CBZ)Lys-Abu-(Acm)Cys-Phe-N₃

D-Trp-(ε-2-Cl-CBZ)Lys-(O-Bzl)Thr-(Acm)Cys-(O-Bzl)Thr-(O-Bzl)Ser-Aha-(ε-2-Cl-CBZ)Lys-Abu-(Acm)Cys-Phe-NH-NH₂ (2.55 g., 1.22 mmole), prepared by the process set forth in Step b), was suspended in 25 ml. freshly degassed DMF. The suspension was stirred magnetically at −40° C. To the suspension was added 1.76 ml. of 5.92N HCl in THF (8.5 equivalents). The resulting clear acidic solution, "pH" 1.0 to 1.5, was warmed to −25° C. and 0.20 ml. isoamyl nitrite (0.135 ml./mmole, 1.2 equivalents) was added and stirring continued for 30 minutes. This solution of D-Trp-(ε-2-Cl-CBZ)Lys-(O-Bzl)Thr-(Acm)Cys-(O-Bzl)Thr-(O-Bzl)Ser-Aha-(ε-2-Cl-CBZ)Lys-Abu-(Acm)Cys-Phe-N₃ was used immediately in Step d).

Step d) - Preparation of Cyclo[Aha-(ε-2-Cl-CBZ)-Lys-Abu-(Acm)Cys-Phe-D-Trp-(ε-2-Cl-CBZ)Lys-(O-Bzl)Thr-(Acm)Cys-(O-Bzl)Thr-(O-Bzl)Ser]

The solution of D-Trp-(ε-2-Cl-CBZ)Lys-(O-Bzl)Thr-(Acm)Cys-(O-Bzl)Thr-(O-Bzl)Ser-Aha-(ε-2-Cl-CBZ)Lys-Abu-(Acm)Cys-Phe-N₃ in DMF, obtained by the process set forth in Step c), was diluted in 1650 ml. freshly degassed DMF, precooled to −40° C. The "pH" was maintained at 7.2 to 7.6 by the addition of 3.02 ml. N,N-diisopropylethylamine. The solution was maintained at −18° C. for 24 hours and then kept at 5° C. for an additional 24 hours during which time 0.55 ml. N,N-diisopropylethylamine was added to maintain the "pH" at 7.2 to 7.6.

The solution was concentrated in vacuo to a thick oil, washed twice with ether and once with ethyl acetate and triturated with water to give a solid. The solid was collected by filtration and dried in vacuo overnight to give 2.28 g. of product.

Step e) - Preparation of Cyclo[Aha-Lys-Abu-(Acm)Cys-Phe-D-Trp-Lys-Thr-(Acm)Cys-Thr-Ser]

Cyclo[Aha-(ε-2-CBZ)Lys-Abu-(Acm)Cys-Phe-D-Trp-(ε-2-Cl-CBZ)Lys-(O-Bzl)Thr-(Acm)Cys-(O-Bzl)Thr-(O-Bzl)Ser] 2.25 g., obtained by the process set forth in Step d), was dissolved in 3 ml. anisole and 25 ml. hydrogen fluoride at dry ice-acetone bath temperature. The solution was stirred magnetically at ice-bath temperature for 1 hour. The excess hydrogen fluoride was removed in vacuo at ice-bath temperature. The resulting oily residue was triturated with ethyl acetate to give a solid. The solid was collected by filtration, washed with ethyl acetate and dried in vacuo to give 1.90 g. of product.

Step f) - Purification of Cyclo[Aha-Lys-Abu-(Acm)Cys-Phe-D-Trp-Lys-Thr-(Acm)Cys-Thr-Ser]

The cyclo[Aha-Lys-Abu-(Acm)Cys-Phe-D-Trp-Lys-Thr-(Acm)Cys-Thr-Ser], 1.29 g., obtained by the process set forth in Step e), was dissolved in 20 ml. 50% aqueous acetic acid and charged to a column of Sephadex G-50, (5 cm. × 115 cm., 2260 ml.) packed in 50% aqueous acetic acid. The column was eluted with 50% aqueous acid at the rate of 15 ml./10 min./fraction. The effluent was monitored at 280 nm.

Fractions 105 to 112 were combined, concentrated to a small volume in vacuo and an equal volume of water added. The solution was lyophilized to give 437 mg. of substantially pure product.

Step g) - Preparation of

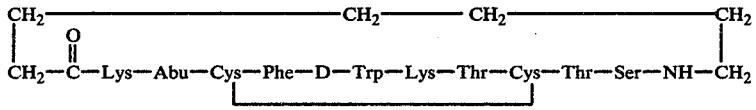

To a solution of 1.23 g. I₂ in 563 ml. acetic acid was added to a solution of 430 mg. cyclo[(Aha-Lys-Abu-(Acm)Cys-Phe-D-Trp-Lys-Thr-(Acm)Cys-Thr-Ser] in 20 ml. 50% acetic acid. The resulting solution was stirred at room temperature for 5 hours. To the reaction solution was added 580 ml. water and the solution extracted with benzene 5 × 600 ml. The 50% acetic acid layer (bottom layer) was concentrated in vacuo to near dryness. The residue was dissolved in 50% acetic acid and charged to a column of Sephadex G-50, (5 cm. × 115 cm., 2260 ml.) packed in 50% aqueous acetic acid. The column was eluted with 50% aqueous acetic acid at the rate of 17 ml./10 min./fraction. The effluent was monitored at 280 nm.

Fractions 104 to 123 were combined, concentrated to dryness in vacuo and the residue lyophilized from 20 ml. 10% aqueous acetic acid to give 309 mg. of product.

A 300 mg. portion of said product was dissolved in 10 ml. 2N acetic acid and charged to a 5 cm. × 115 cm. column packed with Sephadex G-25 in 2N acetic acid and eluted with 2N acetic acid at the rate of 1 ml./min. The effluent was monitored at 254 nm. and 20 ml. fractions were collected.

Fractions 90 to 93 were combined, concentrated to a small volume in vacuo and the residue lyophilized from 2N aqueous acetic acid to give 85 mg. of substantially pure product. A 20 hour acid hydrolysate showed the following amino acid analysis:

|  | μmole/mg. | normalized to average |
| --- | --- | --- |
| Lys | 1.18 | 1.98 |
| Thr | 1.12 | 1.88 |
| Ser | 0.640 | 1.07 |
| Cys | 0.887 | 1.49 |
| Phe | 0.596 | 1.00 |
| Trp | — | — |
| Abu | 0.626 | 1.05 |

EXAMPLE 2

Preparation of

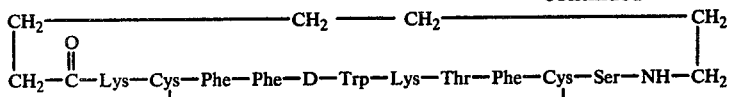

Step a) - Preparation of D—Trp—(ε-2-Cl—CBZ)Lys—(O—Bzl)Thr—Phe—(Acm)Cys—(O—Bzl)Ser—Aha—(ε-2-Cl—CBZ)Lys—(Acm)Cys—Phe—Phe—O—CH$_2$—φ-resin BOC-Phe-O-CH$_2$-φ-resin (2.13 g.; 2.0 mmole), prepared by the process set forth in Example 1, Step a), was carried through the procedures in Tables III of Example 1 and Table IV below using 2 deblockings (2 minutes and 25 minutes) with 25% TFA in methylene chloride (without the presence of ethanedithiol), and 2.5 equivalents of BOC-amino acid in the required sequence until the desired BOC-undeca-peptide-O-CH$_2$-φ-resin was obtained.

DCCI was used as the coupling agent in every step. The coupling of each amino acid proceeded smoothly. Best yields were obtained when the coupling was repeated in each step. When the coupling was repeated, the initial two chloroform washes, the deblocking step and the succeeding three chloroform washes were all omitted and replaced by a single chloroform wash.

The coupling reactions were carried out in methylene chloride, or a mixture of freshly degassed DMF and methylene chloride. The N-terminal amino group was blocked with a BOC group in each case; the hydroxy group of Thr and Ser was blocked with Bzl, the ε-amino group of Lys and 2-Cl-CBZ and the sulfhydryl group of Cys with Acm.

When the desired BOC-undecapeptide-O-CH$_2$-φ-resin was obtained, the N-terminal BOC group was removed by the terminal deblocking procedure set forth in Table V of Example 1.

TABLE VI

| Protected Amino Acid | Solvent ml. |
|---|---|
| BOC-Phe (1.33 g.) | CH$_2$Cl$_2$, 25 ml. |
| recouple | |
| BOC-(Acm)Cys (1.46 g.) | DMF, 5 ml. |
| | CH$_2$Cl$_2$, 20 ml. |
| recouple | |
| BOC-(ε-2-Cl-CBZ)Lys (2.08 g.) | CH$_2$Cl$_2$, 25 ml. |
| recouple | |
| BOC-Aha (1.23 g.) | CH$_2$Cl$_2$, 25 ml. |
| recouple | |
| BOC-(O-Bzl)Ser (1.48 g.) | CH$_2$Cl$_2$, 25 ml. |
| recouple | |
| BOC-(Acm)Cys (1.46 g.) | DMF, 5 ml. |
| | CH$_2$Cl$_2$, 20 ml. |
| recouple | |
| BOC-Phe (1.33 g.) | DMF, 25 ml. |
| recouple | |
| BOC-(O-Bzl)Thr (1.55 g.) | CH$_2$Cl$_2$, 25 ml. |
| recouple | |
| BOC-(ε-2-Cl-CBZ)Lys (2.08 g.) | CH$_2$Cl$_2$, 25 ml. |
| recouple | |
| BOC-D-Trp (1.52 g.) | DMF, 5.5 ml. |
| | CH$_2$Cl$_2$, 19.5 ml. |
| recouple | |

After the sequence of Tables III, V and VI were completed, the blocked undecapeptide-O-CH$_2$-φ-resin was dried overnight in vacuo and weighed 5.50 g.

Step b) - Preparation of D-Trp-(ε-2-Cl-CBZ)Lys-(O-Bzl)Thr-Phe-(Acm)Cys-(O-Bzl)Ser-Aha-(ε-2-Cl-CBZ)Lys-(Acm)Cys-Phe-Phe-NH-NH$_2$ To a mixture of 5.3 g. D-Trp-(ε-2-Cl-CBZ)Lys-(O-Bzl)Thr-Phe-(Acm)Cys-(O-Bzl)Ser-Aha-(ε-2-Cl-CBZ)Lys-(Acm)Cys-Phe-Phe-O-CH$_2$-φ-resin in 53 ml. freshly degassed DMF was added 5.3 ml. NH$_2$-NH$_2$. The mixture was magnetically stirred at room temperature for 1 hour. The mixture was filtered to remove the resin. The resin was washed with 4 × 15 ml. DMF. The filtrate and washings were concentrated in vacuo to an oily residue. The residue was triturated with water to obtain a solid. The solid was collected by filtration and washed with water 8 × to remove formylhydrazide and dried in vacuo 4 days to give 3.23 g. of product.

Step c) - Preparation of D-Trp-(ε-2-Cl-CBZ)Lys-(O-Bzl)Thr-Phe-(Acm)Cys-(O-Bzl)Ser-Aha-(ε-2-Cl-CBZ)Lys-(Acm)Cys-Phe-Phe-N$_3$ D-Trp-(ε-2-Cl-CBZ)Lys-(O-Bzl)Thr-Phe-(Acm)Cys-(O-Bzl)Ser-Aha-(ε-2-Cl-CBZ)Lys-(Acm)Cys-Phe-Phe-NH-NH$_2$ (3.2 g., 1.526 mmole), prepared by the process set forth in Step b), was suspended in 32 ml. freshly degassed DMF. The mixture was stirred magnetically at −25° C. To the mixture was added 1.6 ml. of 4.8N HCl in THF (7.65 mmoles, 5.0 equivalents). To the resulting acidic solution, "pH" 1.5, was added 280λ isoamyl nitrite (2.09 mmoles, 1.37 equivalents) and stirring continued for 30 minutes at −25° C. and then stored at −70° C. The resulting solution of D-Trp-(ε-2-Cl-CBZ)Lys-(O-Bzl)Thr-Phe-(Acm)Cys-(O-Bzl)Ser-Aha-(ε-2-Cl-CBZ)Lys-(Acm)Cys-Phe-Phe-N$_3$ was used immediately in Step d).

Step d) - Preparation of Cyclo[(Acm)Cys-(O-Bzl)-Ser-Aha-(ε-2-Cl-CBZ)Lys-(Acm)Cys-Phe-Phe-D-Trp-(ε-2-Cl-CBZ)Lys-(O-Bzl)Thr-Phe]

The solution of D-Trp-(ε-2-Cl-CBZ)Lys-(O-Bzl)Thr-Phe-(Acm)Cys-(O-Bzl)Ser-Aha-(ε-2-Cl-CBZ)Lys-(Acm)Cys-Phe-Phe-N$_3$ in DMF, obtained by the process set forth in Step c), was diluted in 3200 ml. freshly degassed DMF, precooled to −50° C. The solution was maintained under a nitrogen atmosphere and allowed to warm to −20° C. during which time the "pH" was maintained at 7.2 to 7.6 by the addition of 5.3 ml. N,N-diisopropylethylamine. The solution was maintained at −18° C. for 24 hours and then kept at 5° C. for an additional 24 hours.

The solution was concentrated in vacuo to a thick oil and triturated with 100 ml. water to give a solid. The solid was collected by filtration, slurried with 3 × 50 ml. water and dried in vacuo overnight to give 3.10 g. of product.

Step e) - Preparation of Cyclo[Aha-Lys-(Acm)Cys-Phe-Phe-D-Trp-Lys-Thr-Phe-(Acm)Cys-Ser]

Cyclo[(Acm)Cys-(O-Bzl)Ser-Aha-(ε-2-Cl-CBZ)Lys-(Acm)Cys-Phe-Phe-D-Trp-(ε-2-Cl-CBZ)Lys-(O-Bzl)Thr-Phe], 3.0 g., obtained by the process set forth in Step d), was dissolved in 6 ml. anisole and 60 ml. hydrogen fluoride at dry ice-acetone bath temperature. The solution was stirred magnetically at ice-bath temperature for 1 hour. The excess hydrogen fluoride was removed in vacuo by a water aspirator at ice-bath temperature. The resulting oily residue was maintained in vacuo for an additional 1½ hours by a water aspirator and 3/4 hours by an oil pump at ice-bath temperature and triturated with ethyl acetate to give a solid. The solid was collected by filtration, washed with ethyl acetate (200 ml.) and ether (25 ml.) and dried in vacuo overnight to give 2.78 g. of product.

Step f) - Purification of
Cyclo[Aha-Lys-(Acm)Cys-Phe-Phe-D-Trp-Lys-Thr-Phe-(Acm)Cys-Ser]

The cyclo[Aha-Lys-(Acm)Cys-Phe-Phe-D-Trp-Lyswhich time 30 ml. of freshly prepared 1N $Na_2S_2O_3.5H_2O$ was added. The pale yellow solution was concentrated in vacuo to near dryness. To the residue was added 30 ml. 50% acetic acid and an additional 1 ml. of 1N $Na_2S_2O_3.5H_2O$. Insoluble material was removed by filtration and the filtrate charged to a 5 cm. × 115 cm. column packed with Sephadex G-25 in 50% acetic acid. The column was eluted with 50% acetic acid at a flow rate of 58 ml./hr. and monitored at 254 nm. Fractions of 18.7 ml. were collected.

The product appeared in fractions 64 to 74. Fractions 64 to 72 were combined, evaporated to dryness in vacuo, freeze dried from 25 ml. 10% aqueous acetic acid to give 418.6 mg. of product and subjected to further purification as set forth in Step h).

Step h) - Purification of

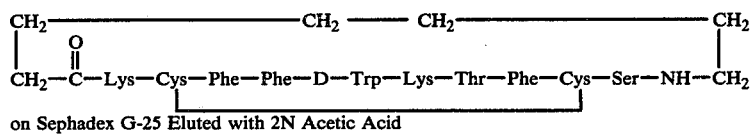

on Sephadex G-25 Eluted with 2N Acetic Acid

Thr-Phe-(Acm)Cys-Ser], 2.78 g., obtained by the process set forth in Step e), was suspended in 35 ml. 50% acetic acid. The suspension was centrifuged to remove insoluble material and the supernatant was charged to a column of Sephadex G-25, (5 cm. × 115 cm., 2260 ml.) packed in 50% aqueous acetic acid. The column was eluted with 50% aqueous acetic acid at a flow rate of 58 ml./hr. The effluent was monitored at 254 nm. Fractions of 18.7 ml. were collected.

Fractions 68 to 83 were combined, concentrated to near dryness in vacuo and the residue lyophilized from 60 ml. 10% aqueous acetic acid to give 1.43 g. of substantially pure product. A 20 hour acid hydrolysate showed the following amino acid analysis:

|  | μmole/mg. | normalized to Phe |
|---|---|---|
| Lys | 1.06 | 1.94 |
| Thr | 0.496 | 0.91 |
| Ser | 0.455 | 0.83 |
| Cys | 0.27 | — |
| Phe | 1.64 | 3.00 |
| Trp | — | — |

Step g) - Preparation of

The product obtained in Step g), 99.2 mg., was dissolved in 5 ml. 2N acetic acid and charged to a 5 cm. × 115 cm. column packed with Sephadex G-25 in 2N acetic acid. The column was eluted with 2N acetic acid at the rate of 1 ml./min. monitoring at 254 nm. Fractions of 18.7 ml. were collected. The product appeared in fractions 97 to 102.

A second portion of product obtained in Step g), weighing 310.2 mg., was charged to a Sephadex G-25 column under identical conditions. The product appeared in fractions 97 to 102.

Fractions 97 to 102 from both columns were combined, concentrated to dryness in vacuo and lyophilized from 20 ml. 10% acetic acid to give 161.1 mg. substantially pure product. A 20 hour acid hydrolysate showed the following amino acid analysis:

|  | μmole/mg. | normalized to Phe |
|---|---|---|
| Lys | 1.27 | 1.97 |
| Thr | 0.622 | 0.97 |
| Ser | 0.619 | 0.96 |
| Cys | 0.892 | 1.39 |
| Phe | 1.93 | 3.00 |
| Trp | — | — |

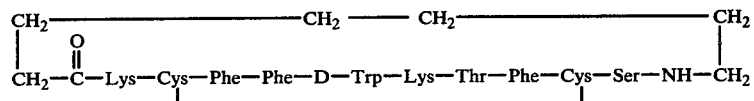

To a solution of 1.53 g. $I_2$ in 700 ml. acetic acid was added a solution of 700 mg., cyclo[Aha-Lys-(Acm)Cys-Phe-Phe-D-Trp-Lys-Thr-Phe-(Acm)Cys-Ser], prepared by the process set forth in Step f), dissolved in 17.5 ml. water and 70 ml. acetic acid. The resulting solution was stirred at room temperature for 5½ hours at

EXAMPLE 3

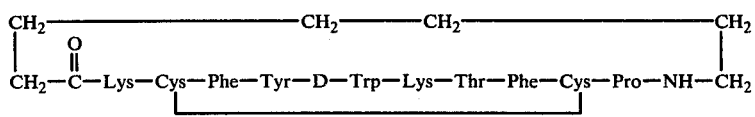

Step a) - Preparation of (O—Bzl)Tyr—D—Trp—(ε-2-Cl—CBZ)Lys—(O—Bzl)Thr—Phe—(Acm)Cys—Pro—Aha—(ε-2-Cl—CBZ)Lys—(Acm)Cys—Phe—O—CH$_2$—φ-resin BOC-Phe-O-CH$_2$-φ-resin (2.13 g.; 2.0 mmole), prepared by the process set forth in Example 1, Step a), was carried through the procedures in Tables III of Example 1 and Table VII below using 2 deblockings (2 minutes and 25 minutes) with 25% TFA in methylene chloride and 2.5 equivalents of BOC-amino acid in the required sequence until the desired BOC-undecapeptide-O-CH$_2$-φ-resin was obtained. During the addition of the last three amino acids in the sequence, the deblocking steps were carried out in the presence of 1% ethanedithiol.

DCCI was used as the sole coupling agent in every step except the coupling of BOC-Pro to Aha-(ε-2-Cl-CBZ)Lys-(Acm)Cys-Phe-O-Ch$_2$-φ-resin in which case the coupling was carried out with DCCI in the presence of 1-hydroxybenzotriazole monohydrate (HBT.H$_2$O).

The coupling of each amino acid proceeded smoothly. Best yields were obtained when the coupling was repeated in each step. When the coupling was repeated, the initial two chloroform washes, the deblocking step and the succeeding three chloroform washes were all omitted and replaced by a single chloroform wash.

The coupling reactions were carried out in methylene chloride, freshly degassed DMF or a mixture of these two solvents. The N-terminal amino group was blocked with a BOC group in each case; the hydroxy group of Thr and Tyr was blocked with Bzl; the ε-amino group of Lys with 2-Cl-CBZ and the sulfhydryl group of Cys with Acm.

When the desired BOC-undecapeptide-O-CH$_2$-φ-resin was obtained, the N-terminal BOC group was removed by the terminal deblocking procedure set forth in Table V.

TABLE VII

| Protected Amino Acid | Solvent ml. |
| --- | --- |
| BOC-(Acm)Cys (1.46 g.) | DMF, 5 ml. CH$_2$Cl$_2$, 20 ml. |
| recouple | |
| BOC-(ε-2-Cl-CBZ)Lys (2.08 g.) | CH$_2$Cl$_2$, 25 ml. |
| recouple | |
| BOC-Aha (1.23 g.) | CH$_2$Cl$_2$, 25 ml. |
| recouple | |
| BOC-Pro (1.08 g.) + HBT.H$_2$O (1.53 g.) | DMF, 25 ml. |
| recouple | |
| BOC-(Acm)Cys (1.46 g.) | DMF, 5 ml. CH$_2$Cl$_2$, 20 ml. |
| recouple | |
| BOC-Phe (1.33 g.) | CH$_2$Cl$_2$, 25 ml. |
| recouple | |
| BOC-(O-Bzl)Thr (1.55 g.) | CH$_2$Cl$_2$, 25 ml. |
| recouple | |
| BOC-(ε-2-Cl-CBZ)Lys (2.08 g.) | CH$_2$Cl$_2$, 25 ml. |
| recouple | |
| BOC-D-Trp (1.52 g.) | DMF, 5.5 ml. CH$_2$Cl$_2$, 19.5 ml. |
| recouple | |
| BOC-(O-Bzl)Tyr (1.86 g.) | CH$_2$Cl$_2$, 25 ml. |

After the sequence of Tables III, V and VII were completed, the blocked undecapeptide-O-CH$_2$-φ-resin was dried overnight in vacuo and weighed 5.21 g.

Step b) - Preparation of (O-Bzl)Tyr-D-Trp-(ε-2-Cl-CBZ)Lys-(O-Bzl)Thr-Phe-(Acm)Cys-Pro-Aha-(ε-2-Cl-CBZ)Lys-(Acm)Cys-Phe-NH-NH$_2$ To a mixture of 5.0 g. (O-Bzl)Tyr-D-Trp-(ε-2-Cl-CBZ)Lys-(O-Bzl)Thr-Phe-(Acm)Cys-Pro-Aha-(ε-2-Cl-CBZ)Lys-(Acm)Cys-Phe-O-CH$_2$-φ-resin in 50 ml. freshly degassed DMF was added 5.0 ml. NH$_2$-NH$_2$. The mixture was magnetically stirred at room temperature for 1 hour. The mixture was filtered to remove the resin. The resin was washed with 4 × 15 ml. DMF. The filtrate and washings were concentrated in vacuo to near dryness. The semi-solid residue was triturated with water to obtain a solid. The solid was collected by filtration, slurried with water to remove all traces of formylhydrazide as determined by a negative reaction of the filtrates to Tollens reagent at room temperature, and dried in vacuo overnight to give 3.04 g. of crude product.

Step c) - Preparation of (O-Bzl)Tyr-D-Trp-(ε-2-Cl-CBZ)Lys-(O-Bzl)Thr-Phe-(Acm)Cys-Pro-Aha-(ε-2-Cl-CBZ)Lys-(Acm)Cys-Phe-N$_3$ (O-Bzl)Tyr-D-Trp-(ε-2-Cl-CBZ)Lys-(O-Bzl)Thr-Phe-(Acm)Cys-Pro-Aha-(ε-2-Cl-CBZ)Lys-(Acm)Cys-Phe-NH-NH$_2$ (2.90 g., 1.37 mmole), prepared by the process set forth in Step b), was suspended in 29 ml. freshly degassed DMF. The suspension was stirred magnetically at −25° C. To the suspension was added 1.06 ml. of 6.44N HCl in THF (6.85 mmoles, 5 equivalents). To the resulting acidic solution, "pH" 1.0 to 1.5, was added 260λ isoamyl nitrite (1.94 mmole, mmole, 1.42 equivalents) and stirring continued for 30 minutes. This solution of (O-Bzl)Tyr-D-Trp-(ε-2-Cl-CBZ)Lys-(O-Bzl)Thr-Phe-(Acm)Cys-Pro-Aha-(ε-2-Cl-CBZ)Lys-(Acm)Cys-Phe-N$_3$ was held at −70° C. and used immediately in Step d).

Step d) - Preparation of Cyclo[Aha-(ε-2-Cl-CBZ)Lys-(Acm)Cys-Phe-(O-Bzl)Tyr-D-Trp-(ε-2-Cl-CBZ)Lys-(O-Bzl)Thr-Phe-(Acm)Cys-Pro]

The solution of (O-Bzl)Tyr-D-Trp-(ε-2-Cl-CBZ)Lys-(O-Bzl)Thr-Phe-(Acm)Cys-Pro-Aha-(ε-2-Cl-CBZ)Lys-(Acm)Cys-Phe-N$_3$ in DMF, obtained by the process set forth in Step c), was diluted in 2870 ml. freshly degassed DMF, precooled to −35° C. The "pH" was maintained at 7.2 to 7.6 by the addition of 6 ml. N,N-diisopropylethylamine. The solution was maintained at −16° C. for 2 days, and at 5° C. for 3 days.

The solution was concentrated in vacuo to a thick oil and triturated with 50 ml. water to give a solid. The solid was collected by filtration, slurried with water (4 × 25 ml.) and dried in vacuo overnight to give 2.93 g. of product.

Step e) - Preparation of Cyclo[Aha-Lys-(Acm)Cys-Phe-Tyr-D-Trp-Lys-Thr-Phe-(Acm)Cys-Pro]

Cyclo[Aha-(ε-2-Cl-CBZ)Lys-(Acm)Cys-Phe-(O-Bzl)Tyr-D-Trp-(ε-2-Cl-CBZ)Lys-(O-Bzl)Thr-Phe-(Acm)Cys-Pro] 2.93 g., obtained by the process set forth in Step d), was suspended in 6 ml. anisole and 6 ml. ethanedithiol. To this mixture was added 60 ml. hydrogen fluoride at dry ice-acetone bath temperature. The solution was stirred magnetically at ice-bath temperature for 1 hour. The excess hydrogen fluoride was removed in vacuo at ice-bath temperature. The resulting oily residue was triturated with ethyl acetate to give a solid. The solid was collected by filtration, washed with ethyl acetate (3 × 10 ml.) and dried in vacuo 24 hours to give 3.68 g. of crude product.

Step f) - Purification of Cyclo[Aha-Lys-(Acm)Cys-Phe-Tyr-D-Trp-Lys-Thr-Phe-(Acm)Cys- Pro]

The cyclo[Aha-Lys-(Acm)Cys-Phe-Tyr-D-Trp-Lys-Thr-Phe-(Acm)Cy-Pro] obtained by the process set forth in Step e), was suspended in 50 ml. 50% aqueous acetic acid. Approximately 0.49 g. insoluble material was removed by filtration. The filtrate was charged to a column of Sephadex G-25, (5 cm. × 115 cm., 2260 ml) packed in 50% aqueous acetic acid. The column was eluted with 50% aqueous acetic acid at the rate of 0.9 ml./min. The effluent was monitered at 254 nm. Fractions of 18.7 ml. were collected.

Fractions 66 to 76 were combined, concentrated to dryness in vacuo and the residue lyophilized from 40 ml. 10% aqueous acetic acid to give 1.5067 g. of product.

The product was dissolved in 25 ml. 2N acetic acid and charged to a 5 cm. × 115 cm. column packed with Sephadex G-25 in 2N acetic acid. The column was eluted with 2N acetic acid and 18.7 ml. cuts were collected. The effluent was monitored at 254 nm.

Fractions 89 to 96 were combined and concentrated in vacuo to dryness. The residue was lyophilized from 20 ml. 10% acetic acid to give 914.6 mg. substantially pure product.

A 20 hour hydrolysate, carried out at 110° C. in aqueous 4N methanesulfonic acid in the presence of 0.2% of 3-(2-aminoethyl)indole, showed the following amino acid composition:

|  | μmole/mg. | normalized to Phe |
|---|---|---|
| Lys | 0.835 | 2.08 |
| Thr | 0.388 | 0.97 |
| Pro | 0.386 | 0.96 |
| Tyr | 0.341 | 0.85 |
| Phe | 0.802 | 2.00 |
| Cys | 0.870 | 2.17 |
| Trp | 0.215 | 0.54 |

Step g) - Preparation of

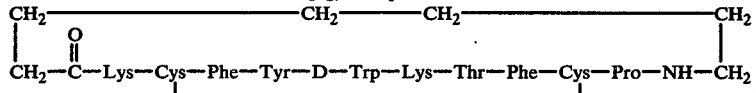

To a solution of 500 mg. cyclo[Aha-Lys-(Acm)Cys-Phe-Tyr-D-Trp-Lys-Thr-Phe-(Acm)Cys-Pro] in 12.5 ml. acetic acid and 50 ml. water, was added a solution of 1.1 g I$_2$ in 500 ml. acetic acid. The resulting solution was kept at room temperature for 5 hours. To the reaction solution was added 550 ml. water and the solution extracted with benzene (5 × 500 ml.) The 50% acetic acid layer (bottom layer) was concentrated in vacuo to near dryness. The oily residue was dissolved in 25 ml. 50% acetic acid and charged to a column of Sephadex G-25, (5 cm. × 115 cm., 2260 ml.) packed in 50% aqueous acetic acid. The column was eluted with 50% aqueous acetic acid at the rate of 0.9 ml./min. The effluent was monitored at 254 nm. Fractions of 18.7 ml. were collected.

Fractions 64 to 69 were combined, concentrated to dryness in vacuo and the residue lyophilized from 20 ml. 10% aqeuous acetic acid to give 257.6 mg. of crude product containing some starting material.

Said crude product was dissolved in 5 ml. 2N acetic acid and charged to a 5 cm. × 115 cm. column packed with Sephadex G-25 in 2N acetic acid and eluted with 2N acetic acid at the rate of 1 ml./min. The effluent was monitored at 254 nm. and 18.7 ml. fractions were collected.

Fractions 97 to 105 were combined, concentrated to dryness in vacuo and the residue lyophilized from 15 ml. 10% aqueous acetic acid to give 168.3 mg. of substantially pure product. A 20 hour acid hydrolysate showed the following amino acid analysis:

|  | μmole/mg. | normalized to Phe |
|---|---|---|
| Lys | 1.23 | 2.02 |
| Thr | 0.610 | 1.0 |
| Pro + Cys | 0.90 | 1.48 |
| ½(Cys)$_2$ | 0.570 | 0.93 |
| Tyr | 0.614 | 1.01 |
| Phe | 1.22 | 2.00 |
| Trp | 0.26 | 0.43 |

Inhibition of Insulin — Inhibition of Glucagon

The relative potencies of somatostatin analogs on the lowering of plasma insulin and glucagon are determined by the following method:

Analogs of somatostatin were compared to somatostatin in their ability to lower the levels of portal vein glucagon and insulin in anesthetized rats. Male Sprague-Dawley rats (Charles River CD) weighing 160–200 grams were anesthetized with urethane (150 mg./100 gm.) Saline or peptides were administered via the external jugular vein. After 5 minutes the portal vein was exposed and blood was collected via syringes containing 3 mg. EDTA and placed in chilled tubes containing 100 μl. of Trasylol (obtained from FBA Pharmaceuticals) for subsequent hormone analysis. Plasma levels of glucagon were determined by the method of Faloona, G. R., and Unger, R. H. "Glucagon" in Methods of Hormone Radioimmunoassay, eds. Jaffe, B. M. and Behrman, H. R. (Academic Press, Inc., New York) Chap. 18 pp. 317–330 (1974) utilizing glucagon antisera 30K. Plasma levels of insulin were determined by a modification of the procedure of Herbert, V., Lau, K. S. Gottlieb, C. W. and Bleicher, S. J., (J. Clin. Endocrin. and Metab.) 25, 1375–1384 (1965).

Inhibition of Pentobarbital Stimulated Growth Hormone Release In Vivo

Somatostatin analogs were compared to somatostatin in their ability to inhibit the release of growth hormone in pentobarbital stimulated rats; a modification of the procedure of Brazeau et al. Endocrinology, 94, 184–187 (1974) was employed. Rats were lightly etherized and sodium pentobarbital (17 mg./Kg. was injected into the exposed Saphenous vein; somatostatin or analog was simultaneously injected subcutaneously. After 15 minutes the animals were bled via the orbital sinus and blood collected for subsequent growth hormone analysis.

Growth Hormone Inhibition In Vitro

Rat pituicytes were isolated according to the procedures of Vale and Grant "In vitro Pituitary Hormone Secretion Assay for Hypophysiotropic Substances" in Methods in Enzymology. Vol. XXXVII, eds. O'Malley, B. W. and Hardman, J. G. (Academic Press, Inc., New York) pp. 5-93 (1975).

After 4 days in culture, the cells were washed and incubated for 4 hours in Dulbecco-modified Eagle's medium in the presence or absence of graded doses of each analog or somatostatin. The medium was then collected for subsequent growth hormone determination by a double antibody radioimmunoassay for rat growth hormone.

Statistical Analysis:

Doses were randomized between groups of animals (6 rats/group). Potency values were determined by four, six, or eight point bioassays with somatostatin as the reference standard. Relative potency values were calculated by a relative potency formula for parallel line bioassays as described in Finney, D. J. Statistical Method in Biological Assay (Charles Griffin and Co., Ltd., London) Chap. 4 pp. 99-138 (1964).

Effect of Somatostatin Analogs on Gastric Secretion

The effect of somatostatin and its analogs on gastric secretion were determined by the following method:

Compounds were tested for their ability to inhibit pentagastrin evoked gastric secretion in the chronic fistula dog. Female beagle dogs with a chronic gastric fistula were given pentagastrin (2.5 µg./kg./hour, i.v. from −60 to 120 min.) and gastric outputs were collected via the fistula cannula. Samples were analyzed at 30 minute intervals for volume (ml.) and titratable acid (mEq/L) (titration to pH with 0.01N NaOH); total acid output (mEq) was calculated as the product of output volume and acid concentration. Test compounds were infused at a constant rate from 0 to 60 minutes. Data have been expressed as percent change of total acid output relative to a placebo trial in the same animals.

The results are as follows:

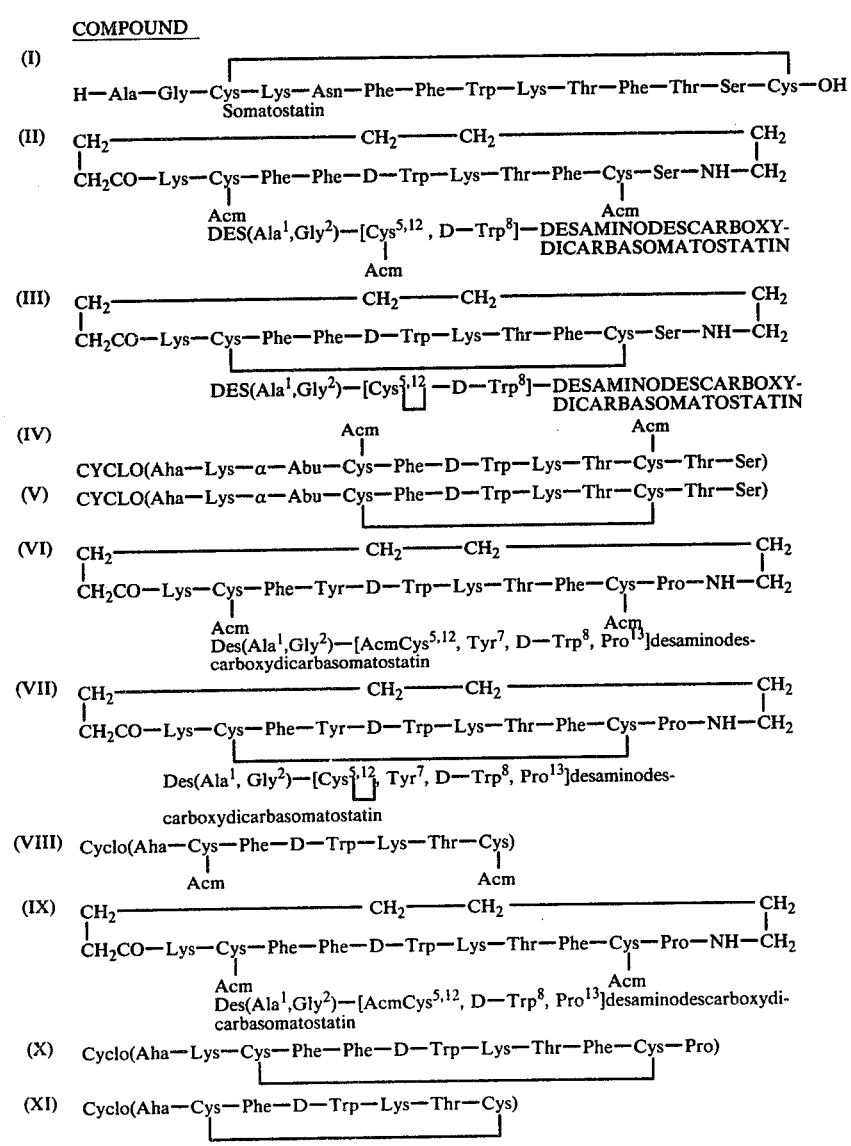

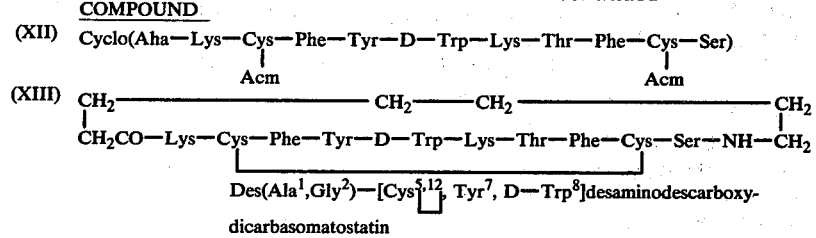

| ACTIVITY OF SELECTED ANALOGS* POTENCY RELATIVE TO SOMATOSTATIN | | | | |
|---|---|---|---|---|
| COMPOUND NO. | Inhibition of Insulin | Inhibition of Glucagon | Inhibition of Pentobarbital Stimulated Growth Hormone Release In Vivo | Growth Hormone Inhibition In Vitro |
| (I) | 1 | 1 | 1 | 1 |
| (II) | 1.62 (0.4–8.8) | 1.16 (0.1–8.4) | | |
| (III) | 1.53 (0.92–2.66) | 1.42 (0.26–12.40) | | |
| (IV) | 0.05 (0.001–0.23) | 0.52 (0.001–3.97) | | |
| | 0.14 (0.05–0.37) | 0.20 (0.02–0.96) | | |
| (V) | 0.91 (0.46–1.86) | 0.99 (0.10–9.59) | 0.87 (0.14–5.2) | |
| | 1.11 (0.64–1.94) | 1.33 (0.28–8.47) | 0.9 (0.1–15.2) | |
| (VI) | 7.4 (4.1–13.3) | 14.5 (6.4–47.8) | 16.2 (8.1–53.8) | 3.5 (2.2–5.6) |
| | 7.5 (4.3–12.5) | 13.4 (4.5–36.2) | 11.5 (3.6–65.8) | 3.1 (1.1–9.2) |
| (VII) | 0.29 (0.17–0.05) | Active no dose response | 0.25 (0.01–0.86) | 0.30 (0.1–0.7) |
| | 0.26 (0.05–0.7) | Low activity non-parallel | 0.3 (non-parallel) | 0.20 (0.12–0.33) |
| (VIII) | <0.03 | Low activity | | 0.03 (0.02–0.05) |
| | | No dose response | 0.14 (0.05–0.29) | 0.14 (0.03–0.46) |
| (IX) | 4.1 (0.6–4.7) | No dose response | Active no dose response | 1.3 (1.0–1.9) |
| | 3.8 (2.2–7.3) | 6.5 (2.2–50.5) | | 1.8 (1.4–2.2) |
| (X) | 0.6 (0.2–1.8) | 0.44 (0.14–1.16) | 0.2 (0.01–1.0) | 0.6 (0.4–1.2) |
| | | | | 0.4 (0.3–0.5) |
| (XI) | 3.5 (2.1–6.4) | 2.7 (1.3–6.1) | | 1.2 (0.8–2.0) |
| | 3.3 (1.8–7.1) | 7.9 (3.2–50) non parallel | | 0.6 (0.5–0.6) |
| (XII) | 1.1 (0.6–2.2) | Active no dose response | | 2.3 (1.7–3.2) |
| | 2.4 (1.0–4.6) | 0.8 (0.2–2.5) | | |
| (XIII) | 0.9 (0.4–1.9) | 2.6 (1.0–18.8) | | 0.9 (0.9–0.9) |
| | 0.7 (0.1–1.9) | 0.9 (0.4–2.3) | | |

| Effect of Somatostatin Analogs on Pentagastrin Evoked Secretion in Chronic Fistula Beagle Dogs Percent Change at 0.8 γ/kg./min. (0–60 min.) | | | | | | | | | |
|---|---|---|---|---|---|---|---|---|---|
| | TITRATABLE ACID | | | | TOTAL ACID OUTPUT | | | | |
| | During | | Post-treat | | During | | | Post-treat | |
| COMPOUND NO. | 0–30 | 30–60 | 60–90 | 90–120 | 0–30 | 30–60 | 60–90 | 90–120 | (N) |
| (I) | −16 | −17 | −61 | −41 | −89 | −99 | −93 | −45 | (8) |
| (II) | −22 | (qns) | −38 | −5 | −94 | −99 | −53 | (+) | (2) |
| (III) | −22 | −70 | −17 | +6 | −80 | −98 | −71 | −24 | (4) |
| (IV) | +15 | +2 | +5 | +1 | +37 | +15 | +100 | +31 | (2) |
| (V) | −11 | +35 | −16 | −4 | −64 | −87 | −88 | −29 | (4) |
| (VI) | −15 | −48 | −20 | −2 | −78 | −91 | −37 | +39 | (4) |
| (VII) | −5 | −11 | +6 | −5 | −47 | −4 | +6 | +6 | (4) |
| (VIII) | | | | | −51 | −37 | 0 | −15 | (2) |
| (IX) | | | | | −90 | −99 | −66 | (+35) | (2) |
| (X) | | | | | −90 | −71 | −11 | (+68) | (2) |
| (XI) | | | | | −85 | −93 | (+27) | −5 | (2) |
| (XII) | | | | | −84 | 98 | −79 | — | (2) |
| (XIII) | — | — | — | — | — | — | — | — | |

The somatostatin analogs of the present invention and the non-toxic pharmaceutically acceptable salts thereof, are useful in humans and animals for inhibiting growth hormone release as in the treatment of acromegaly. They are useful for inhibiting the release of glucagon and alone or in conjunction with insulin, for lowering blood glucose as in the treatment of diabetes. In the treatment of diabetes, the number and size of daily doses and the time of administration are determined by an individual study of each subject. The method of determining these factors is known to those skilled in the art.

The somatostatin analogs described herein may be administered to warm blooded animals, including humans, either intravenously, subcutaneously, intramuscularly or orally. The contemplated dose range for oral administration in tablet or capsule form to large mammals is about 0.001 mg. to about 7 mg./kg. of body weight per day. These somatostatin analogs are preferably administered by injection. A therapeutically effective amount of an analog is ordinarily supplied at a dosage level of from about 0.001 mg. to about 2 mg./kg. of body weight. Preferably the range is from about 0.00142 mg. to about 0.428 mg./kg. of body weight administered by intravenous infusion or by subcutaneous injection. The required dosage will vary with the particular condition being treated, the severity of the condition and the duration of treatment.

If the active ingredient is administered in tablet form, the tablet may contain: a binder such as gum tragacanth, corn starch, gelatin, an excipient such as dicalcium phosphate; a disintegrating agent such as corn starch, and alginic acid; a lubricant such as magnesium stearate;

and a sweetening and/or flavoring agent such as sucrose, lactose and wintergreen. Suitable liquid carriers for intravenous administration include sterile water, isotonic saline and phosphate buffer solutions or other pharmaceutically acceptable injectable carriers.

The following example is included to illustrate the preparation of a representative dose of

```
CH2————————————CH2————————CH2————————————————CH2
 |     O                                              |
 |     ‖                                              |
CH2—C—Lys—Abu—Cys—Phe—D—Trp—Lys—Thr—Cys—Thr—Ser—NH—CH2
                └─────────────────────────┘
``` suitable for subcutaneous injection.

EXAMPLE 4

1 ml.        sterile saline;
1 mg.

```
CH2————————————CH2————————CH2————————————————CH2
 |     O                                              |
 |     ‖                                              |
CH2—C—Lys—Abu—Cys—Phe—D—Trp—Lys—Thr—Cys—Thr—Ser—NH—CH2
                └─────────────────────────┘
```

What is claimed is:

1. The compounds having the formula:

```
CH2————————————————————CH2—
 |                      O
 |                      ‖
CH2—C—A—B—NH—CH—C—C—D— or
                |
               CH2————X——

—CH2————————————————————CH2
                O
                ‖
L—Trp)—Lys—E—NH—CH—C—F—G—NH—CH—R
                              |
—Y————————————CH2

O
            ‖
            C————————
            |
           NH          O
                       ‖
NH2—(CH2)4—CH—C—NH—CH—C—Phe—C—(D— or
              ‖       |
              O      CH2————X——

—(CH2)m——————————————————————CH—R
                              |
                              O
                              |
L—Trp)—Lys—E—Phe—NH—CH—C—G—NH
                         |
—Y————————————CH2
``` wherein,
R is H or COOH, m is 0 to 9,
A is (Lys)$_n$,
B is (Asn)$_p$, Abu, Pro or Ala,
C is Phe or Tyr,
E is Thr or Val,
F is (Thr)$_q$ or Val, G is (Ser)$_r$, Pro, Ala or Gly, and
X and Y are independently CH2—S or S wherein n, p, q and r are 0 or 1 and pharmaceutically acceptable non-toxic acid addition salts thereof.

2. The compounds having the formula:

```
CH2————————————————————————CH2—
 |     O                    O
 |     ‖                    ‖
CH2—C—A—B—NH—CH—C—C—(D— or
                |
               CH2————X——

—CH2————————————————————CH2
                O
                ‖
L—Trp)—Lys—E—NH—CH—C—F—G—NH—CH—R

—Y————————————CH2
``` wherein,
R is H or COOH,
A is (Lys)$_n$,
B is (Asn)$_p$, Abu, Pro or Ala,
C is Phe or Tyr,
E is Thr or Val,
F is (Thr)$_q$ or Val,
G is (Ser)$_r$, Pro, Ala or Gly, and
X and Y are independently CH2—S or S wherein n, p, q and r are 0 or 1 and pharmaecutically acceptable non-toxic acid addition salts thereof.

3. The compounds according to claim 2 wherein n, p, q and r are o.

4. The compounds having the formula:

```
            O
            ‖
            C————————————————(CH2)m————————————————————CH—R
            |                                           |
           NH          O                                O
            |          ‖                                ‖
NH2—(CH2)4—CH—C—NH—CH—C—Phe—C—(D—or L—Trp)—Lys—E—Phe—NH—CH—C—G—NH
              ‖       |                                           |
              O      CH2————X————Y————————————————————CH2
``` wherein,
R is H or COOH,
m is 0 to 9,
C is Phe or Tyr, E is Val or Thr,

G is Ser, Pro, Ala or Gly, and

X and Y are independently CH₂—S or S
and pharmaceutically acceptable non-toxic acid addition salts thereof.

5. The compounds according to claim 2 having the formula:

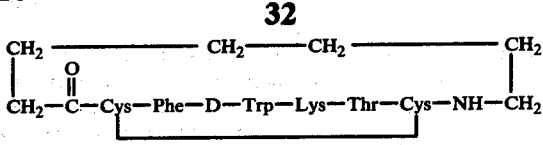

and pharmaceutically acceptable non-toxic acid addition salts thereof.

| COMPOUND NO. | Inhibition of Insulin | Inhibition of Glucagon | Inhibition of Pentobarbital Stimulated Growth Hormone Release In Vivo | Growth Hormone Inhibition In Vitro |
|---|---|---|---|---|
| (I) | 1 | 1 | 1 | 1 |
| (II) | 1.62 (0.4–8.8) | 1.16 (0.1–8.4) | | |
| (III) | 1.53 (0.92–2.66) | 1.42 (0.26–12.40) | | |
| (IV) | 0.05 (0.001–0.23) | 0.52 (0.001–3.97) | | |
|  | 0.14 (0.05–0.37) | 0.20 (0.02–0.96) | | |
| (V) | 0.91 (0.46–1.86) | 0.99 (0.10–9.59) | 0.87 (0.14–5.2) | |
|  | 1.11 (0.64–1.94) | 1.33 (0.28–8.47) | 0.9 (0.1–15.2) | |
| (VI) | 7.4 (4.1–13.3) | 14.5 (6.4–47.8) | 16.2 (8.1–53.8) | 3.5 (2.2–5.6) |
|  | 7.5 (4.3–12.5) | 13.4 (4.5–36.2) | 11.5 (3.6–65.8) | 3.1 (1.1–9.2) |
| (VII) | 0.29 (0.17–0.05) | Active no dose response | 0.25 (0.01–0.86) | 0.30 (0.1–0.7) |
|  | 0.26 (0.05–0.7) | Low activity non-parallel | 0.3 (non-parallel) | 0.20 (0.12–0.33) |
| (VIII) | <0.03 | Low activity | | 0.03 (0.02–0.05) |
|  | | No dose response | 0.14 (0.05–0.29) | 0.14 (0.03–0.46) |
| (IX) | 4.1 (0.6–4.7) | No dose response | Active no dose response | 1.3 (1.0–1.9) |
|  | 3.8 (2.2–7.3) | 6.5 (2.2–50.5) | | 1.8 (1.4–2.2) |
| (X) | 0.6 (0.2–1.8) | 0.44 (0.14–1.16) | 0.2 (0.01–1.0) | 0.6 (0.4–1.2) |
|  | | | | 0.4 (0.3–0.5) |
| (XI) | 3.5 (2.1–6.4) | 2.7 (1.3–6.1) | | 1.2 (0.8–2.0) |
|  | 3.3 (1.8–7.1) | 7.9 (3.2–50) non parallel | | 0.6 (0.5–0.6) |
| (XII) | 1.1 (0.6–2.2) | Active no dose response | | 2.3 (1.7–3.2) |
|  | 2.4 (1.0–4.6) | 0.8 (0.2–2.5) | | |
| (XIII) | 0.9 (0.4–1.9) | 2.6 (1.0–18.8) | | 0.9 (0.9–0.9) |
|  | 0.7 (0.1–1.9) | 0.9 (0.4–2.3) | | | and pharmaceutically acceptable non-toxic acid addition salts therof.

6. The compound according to claim 4 having the formula:

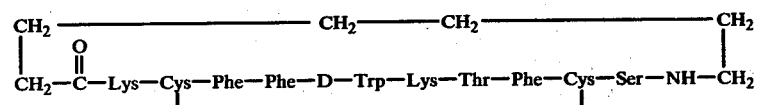

and pharmaceutically acceptable non-toxic acid addition salts thereof.

7. The compound according to claim 4 having the formula:

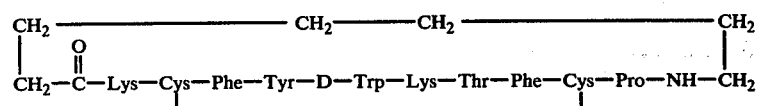

and pharmaceutically acceptable non-toxic acid addition salts thereof.

8. The compound according to claim 2 having the formula:

9. The compounds having the formula:

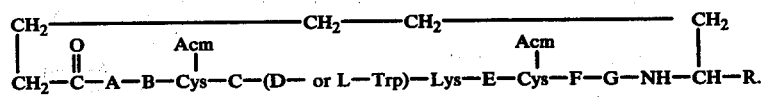

wherein,
R is H or COOH,
A is (Lys)$_n$,
B is (Asn)$_p$, Abu, Pro or Ala,
C is Phe or Tyr,
E is Thr or Val,
F is (Thr)$_q$ or Val,
G is (Ser)$_r$, Pro, Ala or Gly, and
X and Y are independently CH₂—S—
wherein n, p, q and r are 0 or 1 and pharmaceutically acceptable non-toxic acid addition salts thereof.

10. The compounds having the formula:

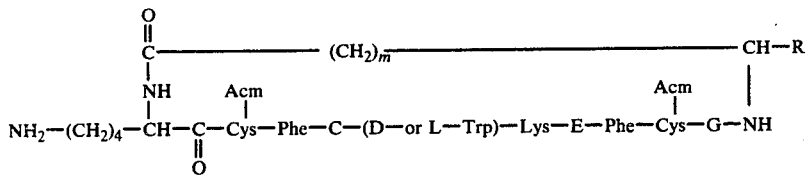

wherein,
R is H or COOH,
m is 0 to 9,
C is Phe or Tyr,
E is Val or Thr,
G is Ser, Pro, Ala or Gly and
pharmaceutically acceptable non-toxic acid addition salts thereof.

11. A pharmaceutical composition comprising a therapeutically effective amount of the peptide having the structures:

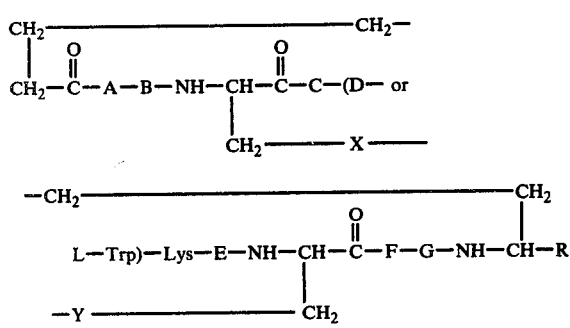

wherein,
R is H or COOH,
m is 0 to 9,
A is $(Lys)_n$,
B is $(Asn)_p$, Abu, Pro or Ala,
C is Phe or Tyr,
E is Thr or Val,
F is $(Thr)_q$ or Val,
G is $(Ser)_r$, Pro, Ala or Gly, and
X and Y are independently $CH_2$—S or S
wherein n, p, q and r are 0 or 1 and non-toxic acid addition salts therein in a pharmaceutically acceptable liquid or solid carrier.

12. A pharmaceutical composition comprising a therapeutically effective amount of the peptide having the structure:

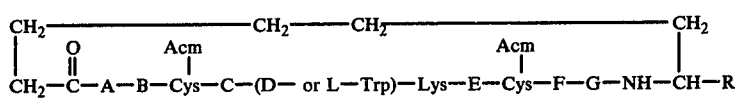

wherein,
R is H or COOH,
A is $(Lys)_n$,
B is $(Asn)_p$, Abu, Pro or Ala,
C is Phe or Tyr,
E is Thr or Val,
F is $(Thr)_q$ or Val,
G is $(Ser)_r$, Pro, Ala or Gly, and
X and Y are independently $CH_2$—S or S
wherein n, p, q and r are 0 or 1 and non-toxic acid addition salts thereof in a pharmaceutically acceptable liquid or solid carrier.

13. A pharmaceutical composition comprising a therapeutically effective amount of the peptide having the structure:

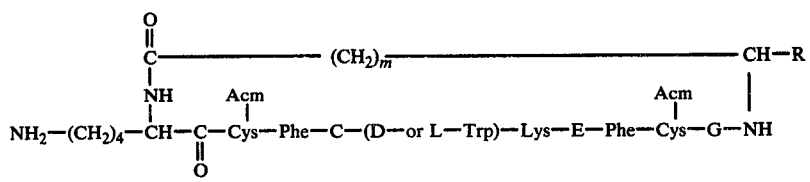

wherein
R is H or COOH,
m is 0 to 9,
C is Phe or Tyr,
E is Val or Thr,
G is Ser, Pro, Ala or Gly and
non-toxic acid addition salts thereof in a pharmaceutically acceptable liquid or solid carrier.

* * * * *

UNITED STATES PATENT OFFICE
CERTIFICATE OF CORRECTION

Patent No. 4,139,526            Dated February 13, 1979

Inventor(s) Daniel F. Veber

It is certified that error appears in the above-identified patent and that said Letters Patent are hereby corrected as shown below:

In column 33, between lines 35 and 50 the below structure for claim 11 was omitted.

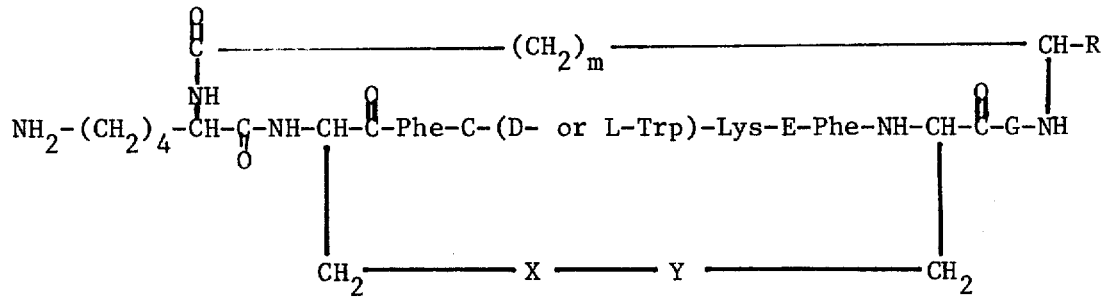

Signed and Sealed this

Seventeenth Day of July 1979

[SEAL]

Attest:

LUTRELLE F. PARKER
*Attesting Officer*     *Acting Commissioner of Patents and Trademarks*